(12) United States Patent
Murakami et al.

(10) Patent No.: US 11,324,842 B2
(45) Date of Patent: May 10, 2022

(54) LIGHT IRRADIATION DEVICE

(71) Applicant: Ushio Denki Kabushiki Kaisha, Tokyo (JP)

(72) Inventors: Satoshi Murakami, Tokyo (JP); Yoshihiro Kanahashi, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 118 days.

(21) Appl. No.: 17/018,100

(22) Filed: Sep. 11, 2020

(65) Prior Publication Data

US 2021/0077641 A1     Mar. 18, 2021

(30) Foreign Application Priority Data

Sep. 13, 2019    (JP) .............................. JP2019-167772

(51) Int. Cl.
     *A61L 2/08*        (2006.01)
     *G01F 1/37*        (2006.01)
     *A61L 2/10*        (2006.01)

(52) U.S. Cl.
CPC    *A61L 2/08* (2013.01); *A61L 2/10* (2013.01); *G01F 1/37* (2013.01); *A61L 2202/122* (2013.01)

(58) Field of Classification Search
CPC ........ A61L 2/08; A61L 2/10; A61L 2202/122; A61L 2202/11; G01F 1/37

USPC ..................................................... 250/455.11
See application file for complete search history.

(56) References Cited

U.S. PATENT DOCUMENTS

2017/0095818 A1*   4/2017   Liu ................... B01L 3/502723

FOREIGN PATENT DOCUMENTS

JP        2017-143971 A     8/2017

\* cited by examiner

*Primary Examiner* — Kiet T Nguyen
(74) *Attorney, Agent, or Firm* — Studebaker & Brackett PC

(57) ABSTRACT

The light irradiation device includes a light source supporter having a tubular shape is closed on a side of one end, a plurality of light-emitting elements placed on an outer wall surface of the light source supporter, a tubular body extending inside the light source supporter in an axial direction of the light source supporter, a first flow channel formed between the tubular body and the light source supporter and having an annular shape when viewed from the axial direction; and a second flow channel formed inside the tubular body, wherein the first flow channel and the second flow channel communicate with each other on a side of one end of the light source supporter, and the tubular body contains a material having a thermal conductivity lower than a thermal conductivity of a material constituting an outer wall of the first flow channel.

18 Claims, 8 Drawing Sheets

LIGHT IRRADIATION DEVICE

BACKGROUND OF THE INVENTION

Field of the Invention

The present invention relates to a light irradiation device, particularly relates to a light irradiation device that applies light with LED elements.

Description of the Related Art

As a light source for sterilizing a fluid in a container or tank or for photochemical treatment, for example, a long light irradiation device as disclosed in the following Patent Document 1, which includes a plurality of LEDs as a light source and extends in one direction, is known.

PRIOR ART DOCUMENT

Patent Document

Patent Document 1: JP-A-2017-143971

SUMMARY OF THE INVENTION

The present inventors have studied such a light irradiation device as described above for use in sterilizing a fluid in a container or tank or for photochemical treatment, and as a result, have found that the light irradiation device has a problem as described below. Hereinbelow, a description will be made with reference to the drawings.

When electric power is supplied to an LED, the LED emits light and generates heat, and therefore the temperature of the LED gradually increases. However, the luminous efficacy of the LED decreases as the temperature of the LED increases. For this reason, most of light irradiation devices having LEDs as a light source have a cooling mechanism.

For example, a rod-shaped long light irradiation device such as the light irradiation device disclosed in Patent Document 1 has a cooling mechanism configured to allow cooling water to flow through a flow channel formed inside a light source supporter on which LEDs as a light source are placed.

FIG. 10 is a schematic sectional side view of a light irradiation device 100 having a conventional structure, and FIG. 11 is a schematic sectional view of the light irradiation device 100 shown in FIG. 10 taken along an XY plane at a predetermined Z coordinate. As shown in FIG. 10 and FIG. 11, the conventional light irradiation device 100 has a second flow channel F20 configured to allow cooling water W10 to flow therethrough and a first flow channel F10 configured to allow cooling water W20 to flow therethrough toward an outlet so that the cooling water W20 absorbs the heat of LEDs 111. In the following description, the axial direction of a light source supporter 110 is defined as a Z direction, and a plane orthogonal to the Z direction is defined as an XY plane.

In this description, when a distinction is made between a positive direction and a negative direction to express a direction, a positive or negative sign is given like "+Z direction" or "−Z direction". When a direction is expressed without making a distinction between a positive direction and a negative direction, the term "direction" is simply used like "Z direction".

In the cooling mechanism having such a structure, the cooling water W10 flows through the second flow channel F20, and then the cooling water W20 flows through the first flow channel F10 while absorbing heat from the LEDs 111. The temperature of the cooling water W20 has increased by heat absorbed from the LEDs 111, and therefore the temperature of the cooling water W10 flowing through the second flow channel F20 increases due to the transfer of heat through a tubular body 112.

For this reason, the temperature of the cooling water W10 flowing through the second flow channel F20 has already increased before absorption of heat from the LEDs 111, which makes it difficult to absorb heat from the LEDs 111 and reduces the efficiency of cooling the LEDs 111. As the result, the luminous efficacy of the LEDs 111 may be reduced and the illuminance of the light irradiation device 100 may be reduced.

In view of the above problem, it is an object of the present invention to provide a light irradiation device having improved cooling efficiency.

The present invention is directed to a light irradiation device including:

a light source supporter having a tubular shape is closed on a side of one end;

a plurality of light-emitting elements placed on an outer wall surface of the light source supporter;

a tubular body extending inside the light source supporter in an axial direction of the light source supporter;

a first flow channel formed between the tubular body and the light source supporter and having an annular shape when viewed from the axial direction; and a second flow channel formed inside the tubular body, wherein the first flow channel and the second flow channel communicate with each other on a side of one end of the light source supporter, and the tubular body contains a material having a thermal conductivity lower than a thermal conductivity of a material constituting an outer wall of the first flow channel.

Such a structure allows a material having a thermal conductivity lower than that of a material constituting the outer wall of the first flow channel to interpose between the first flow channel and the second flow channel. This suppresses the transfer of heat between a cooling medium flowing through the first flow channel, such as water, and the cooling medium flowing through the second flow channel.

That is, the cooling medium flowing through the second flow channel is less likely be heated by the cooling medium flowing through the first flow channel. Therefore, the above-described structure allows the cooling medium to flow through the second flow channel while keeping a lower temperature as compared with the conventional structure, which improves cooling efficiency.

It is to be noted that the material interposed between the first flow channel and the second flow channel is not particularly limited as long as the material has a thermal conductivity lower than that of a material constituting the outer wall of the first flow channel, and may be a gaseous material or a liquid material.

Further, the cooling medium may be discharged after flowing through the first flow channel and then through the second flow channel, or may be discharged after flowing through the second flow channel and then through the first flow channel.

In the light irradiation device, a gap may be interposed between the first flow channel and the second flow channel.

The thermal conductivity of air is much lower than that of a metal, and is lower than that of water, a resin, or wood. Therefore, such a structure as described above in which a gap is interposed between the first flow channel and the second flow channel makes it possible to further suppress the transfer of heat of the cooling medium flowing through the first flow channel to the cooling medium flowing through the second flow channel. It is to be noted that the gap is preferably formed throughout the tubular body in the axial direction, but may be formed in part of the tubular body.

The light irradiation device may further include a plurality of supporting projections formed so as to project from the light source supporter toward the tubular body or from the tubular body toward the light source supporter.

When the light irradiation device is used for a long period of time, an area where the cooling medium does not flow may be created in the first flow channel formed between the light source supporter and the tubular body provided inside the light source supporter because the light source supporter and the tubular body come into direct contact with each other due to the flexure or thermal expansion deformation of the light source supporter and the tubular body. When this occurs, heat generated by the LEDs cannot locally be absorbed, and some of the light-emitting elements may be reduced luminous efficacy, turn off, and then break.

However, such a structure as described above makes it possible, even when the flexure or deformation of the light source supporter and the tubular body occurs, to keep a certain distance between the light source supporter and the tubular body because the tips of the supporting projections come into contact with the outer wall surface of the tubular body. This makes it possible to prevent the creation of an area where the cooling medium does not flow. It is to be noted that, as described above, the supporting projections may project from the tubular body toward the light source supporter.

In the light irradiation device, a number of the supporting projections as viewed in the axial direction may be at least three.

Such a structure makes it possible, even when the light source supporter and the tubular body deform in any direction, to support the light source supporter and the tubular body to maintain the flow channel. Further, when viewed in the axial direction of the light source supporter, the at least three supporting projections are preferably arranged so that the adjacent supporting projections are spaced at an angle of 120 degrees in a circumferential direction around the axis of the light source supporter.

In the light irradiation device, the tubular body may include an inner tubular body having the second flow channel formed therein and an outer tubular body provided so as to surround the inner tubular body.

When the tubular body is configured so that the inner tubular body and the outer tubular body are spaced from each other, an gap can easily be interposed between the first flow channel and the second flow channel throughout the tubular body.

The light irradiation device may further include a plurality of gap-maintaining parts formed so as to project from the inner tubular body toward the outer tubular body or from the outer tubular body toward the inner tubular body.

When the flexure or thermal expansion deformation of the inner tubular body and the outer tubular body occurs, the inner tubular body and the outer tubular body come into direct contact with each other without an gap being interposed between the outer tubular body and the inner tubular body provided inside the outer tubular body so that an area having a high thermal conductivity is created.

However, such a structure as described above makes it possible, even when the flexure or deformation of the inner tubular body and the outer tubular body of the tubular body occurs, to keep a certain distance between the inner tubular body and the outer tubular body because the tips of the gap-maintaining parts come into contact with the inner wall surface of the outer tubular body. This makes it possible to interpose an gap between the first flow channel and the second flow channel throughout the tubular body while minimizing the area of direct contact between the inner tubular body and the outer tubular body. It is to be noted that, as described above, the gap-maintaining parts may project from the outer tubular body toward the inner tubular body.

In the light irradiation device, a number of the gap-maintaining parts as viewed in the axial direction may be at least three.

Such a structure also makes it possible, even when the light source supporter and the tubular body deform in any direction, to maintain the gap by the gap-maintaining parts similarly to the above-described supporting projections. Further, when viewed in the axial direction of the light source supporter, the at least three gap-maintaining parts are preferably arranged so that the adjacent gap-maintaining parts are spaced at an angle of 120 degrees in a circumferential direction around the axis of the light source supporter.

The light irradiation device may further include a holding member having a function of fixing the light source supporter and the tubular body at an end opposite to the one end of the light source supporter and relieving a thermal expansion difference in the axial direction between the inner tubular body and the outer tubular body.

In the light irradiation device, the holding member may have a sliding mechanism configured to allow the inner tubular body and the outer tubular body to be displaced along the axial direction.

In the light irradiation device, the holding member may have an elastic member to allow the inner tubular body and the outer tubular body to be displaced along the axial direction.

When the light-emitting elements light up, the light source supporter and the tubular body thermally expand due to heat generated by the light-emitting elements. At this time, thermal expansion in the radial direction of the light source supporter slightly changes the flow channel cross-sectional areas of the first flow channel and the second flow channel but does not have an great impact, but thermal expansion in the axial direction of the light source supporter puts a load on the holding member fixing the light source supporter and the tubular body. Particularly, when a thermal expansion difference between the inner tubular body and the outer tubular body of the tubular body is large, and displacement in the axial direction of the light source supporter increases so that the holding member may breaks.

However, such a structure as described above makes it possible to relieve a thermal expansion difference between the inner tubular body and the outer tubular body to reduce a load put on the holding member, thereby reducing the frequency of exchanging the member.

The holding member is preferably made of a material having a certain degree of elasticity. For example, a synthetic resin such as a fluorine resin or polytetrafluoroethylene may be used. The elastic member may be, for example, a synthetic rubber such as a fluorine-containing rubber or a silicone resin. It is to be noted that there is a case where friction occurs between the holding member and the tubular member when the tubular member slides due to thermal expansion. In order to prevent the tubular body from being scratched at this time, the holding member is preferably made of a material softer than a material constituting the tubular body.

In the light irradiation device, the outer wall of the first flow channel, the inner tubular body, and the outer tubular body may be made of the same material.

When the outer wall of the first flow channel, the inner tubular body, and the outer tubular body are made of the same material, these members have the same coefficient of thermal expansion, and therefore the light source supporter constituting the outer wall of the first flow channel, the inner tubular body, and the outer tubular body thermally expand in the same way. Therefore, there is not a large difference in deformation among the outer wall and inner wall of the first flow channel, the inner tubular body, and the outer tubular body. As described above, this makes it possible to prevent the members from easily coming into direct contact with each other and to reduce a local load put on the device.

Further, when the members are made of the same material, the light irradiation device can entirely be integrally formed by welding or the like, which reduces the number of joints or connections between the members. This makes it possible to reduce or eliminate the need for taking measures against the leakage of the cooling medium and the need for a periodic inspection. Further, when the members are made of a metal, the use of the same metal is effective at preventing electrolytic corrosion.

The outer wall of the first flow channel and the tubular body are preferably made of a material having a high thermal conductivity and being harder than a material constituting the holding member. For example, copper, stainless steel, or titanium may be used.

In the light irradiation device, a flow channel cross-sectional area of the first flow channel as viewed in the axial direction may be smaller than a flow channel cross-sectional area of the second flow channel as viewed in the axial direction.

The cooling efficiency of the cooling medium increases as the flow velocity of the cooling medium increases. Heat generated by the light-emitting elements is mainly absorbed by the cooling medium flowing through the first flow channel formed on the outer side. Therefore, in order to improve the cooling efficiency, the flow velocity of the cooling medium flowing through the first flow channel needs to be fast.

Such a structure as described above makes the flow velocity of the cooling medium flowing through the first flow channel faster than the flow velocity of the cooling medium flowing through the second flow channel so that the efficiency of cooling the light-emitting elements improves.

According to the present invention, it is possible to achieve a light irradiation device having improved cooling efficiency.

DETAILED DESCRIPTION OF THE PREFERRED EMBODIMENTS

Hereinbelow, a light irradiation device according to the present invention will be described with reference to the drawings. It is to be noted that all the drawings are schematically shown, and the size ratio between components and the number of components in each of the drawings are not always the same as the actual size ratio and number.

Figure 1:
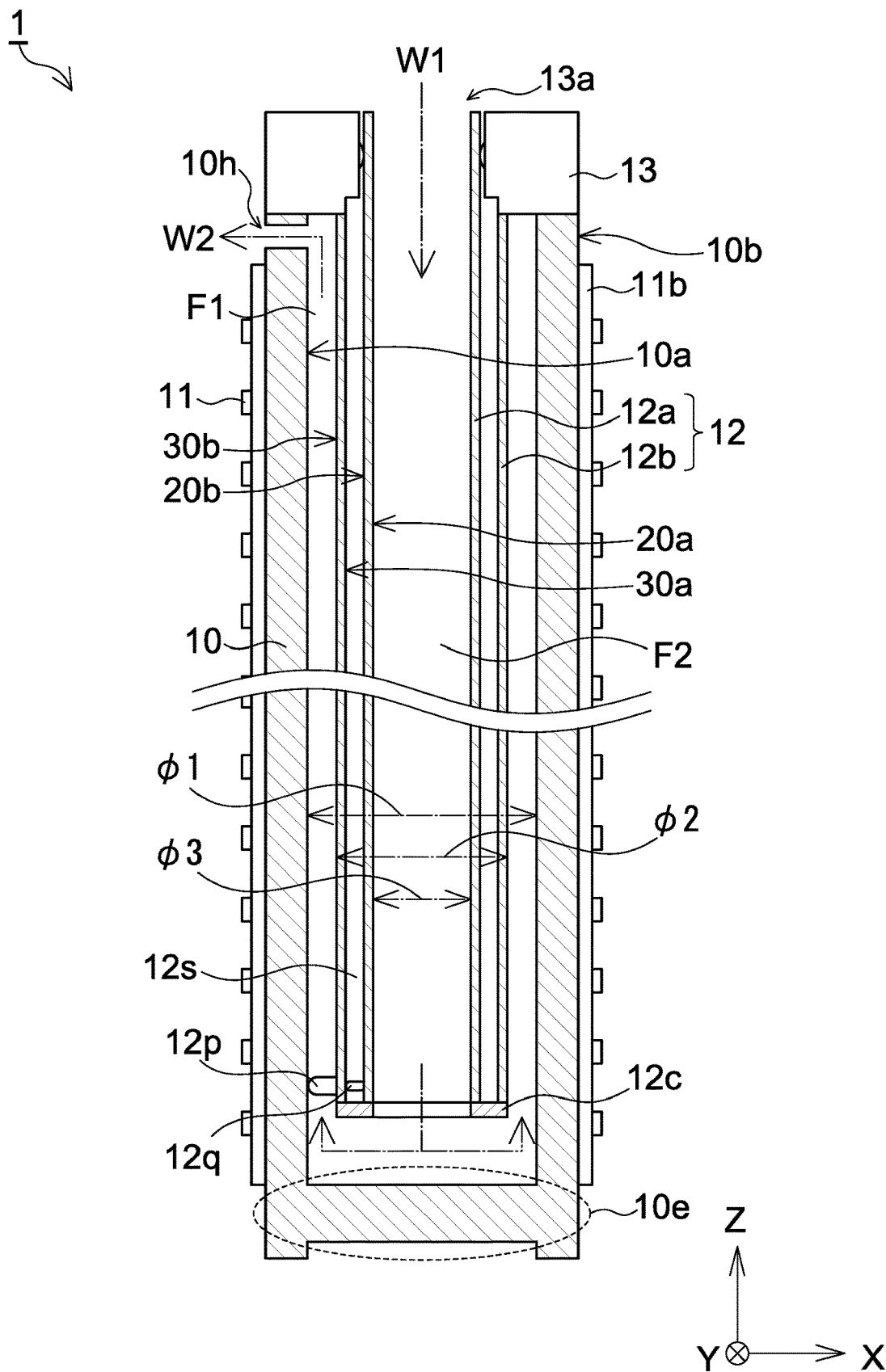
FIG. 1 is a schematic sectional side view of an embodiment of a light irradiation device.
Figure 2:
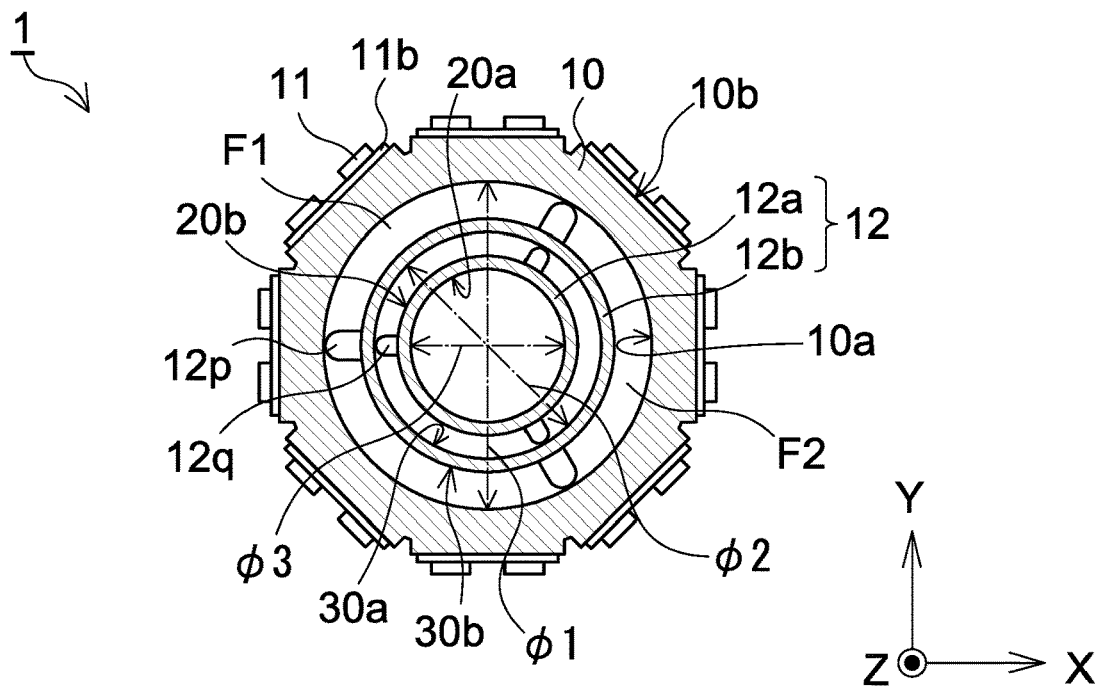
FIG. 2 is a sectional view of the light irradiation device shown in FIG. 1 taken along an XY plane at a predetermined Z coordinate.

FIG. 1 is a schematic sectional side view of an embodiment of a light irradiation device 1. FIG. 2 is a sectional view of the light irradiation device 1 shown in FIG. 1 taken along an XY plane at a predetermined Z coordinate. Similarly to the above description, also in the following description, the axial direction of a light source supporter 10 is defined as a Z direction, and a plane orthogonal to the Z direction is defined as an XY plane. When a distinction is made between a positive direction and a negative direction to express a direction, a positive or negative sign is given like "+Z direction" or "−Z direction", and when a direction is expressed without making a distinction between a positive direction and a negative direction, the term "direction" is simply used like "Z direction".

As shown in FIG. 1 and FIG. 2, the light irradiation device 1 includes a light source supporter 10, a plurality of light-emitting elements 11 provided on an outer wall surface 10b of the light source supporter 10, a tubular body 12 provided inside the light source supporter 10, and a holding member 13 holding the light source supporter 10 and the tubular body 12.

The light source supporter 10 is tubular and has the outer wall surface 10b and an inner wall surface 10a. When the light source supporter 10 is viewed in the Z direction, the outer wall surface 10b has a regular octagonal shape, and the inner wall surface 10a has a circular shape. The light source supporter 10 is closed on an end 10e side in the −Z direction. On each of the faces of the outer wall surface 10b, a substrate 11b is provided to place the light-emitting elements 11 thereon. Although not shown in the drawings, the substrate 11b has wiring for supplying electric power to allow the light-emitting elements 11 to emit light.

The light-emitting elements 11 of the present embodiment are LEDs, but may be, for example, other light-emitting elements such as LDs or phosphors. Alternatively, these different light-emitting elements may be mixed. When the light source supporter 10 of the present embodiment is viewed in the Z direction, the outer wall surface 10b has a regular octagonal shape, but may have another polygonal shape or a circular shape.

On the inside of the light source supporter 10, the tubular body 12 is provided. The light source supporter 10 and the tubular body 12 are fixed by the holding member 13 on a side opposite to the end 10e, that is, on an end side in the +Z direction. The tubular body 12 includes an inner tubular body 12a constituting an inner wall surface 20a and an outer tubular body 12b constituting an outer wall surface 30b. The inner tubular body 12a and the outer tubular body 12b are connected to each other by a connecting member 12c on the end 10e side of the light source supporter 10, and an air gap 12s is provided between the inner tubular body 12a and the outer tubular body 12b.

As shown in FIG. 1 and FIG. 2, a first flow channel F1 is formed between the inner wall surface 10a of the light source supporter 10 and the outer tubular body 12b so that cooling water W2 flows therethrough in the +Z direction toward an outlet 10h while absorbing heat from the light-emitting elements 11. The first flow channel F1 has an annular shape when viewed in the Z direction. On the inside of the inner tubular body 12a, a second flow channel F2 is formed so that cooling water W1 supplied from the outside as a cooling medium flows therethrough in the −Z direction. The second flow channel F2 has a circular shape when viewed in the Z direction. It is to be noted that in this description, water is used as a cooling medium, but any cooling medium may be used as long as it is a fluid having a cooling function.

The outer tubular body 12b constituting the tubular body 12 has supporting projections 12p formed so as to project toward the light source supporter 10. As shown in FIG. 2, three supporting projections 12p are formed, and are spaced at regular intervals in a circumferential direction around the axis of the light source supporter 10 when the light source supporter 10 is viewed in the Z direction.

The supporting projections 12p are configured so that only the tips thereof come into contact with the inner wall surface 10a of the light source supporter 10 to prevent the inner wall surface 10a of the light source supporter 10 and the outer wall surface 30b of the outer tubular body 12b from coming into direct contact with each other over a large area when the tubular body 12 is deformed by, for example, flowing of the cooling water (W1, W2) or thermal expansion. That is, the supporting projections 12p support the tubular body 12 to prevent a situation in which, when the first flow channel F1 is viewed in the Z direction, part of the first flow channel F1 is extremely wide or extremely narrow or closed in a circumferential direction around the axis of the light source supporter 10.

It is to be noted that the number of the supporting projections 12p is not particularly limited, and the supporting projections 12p do not necessarily have to be spaced at regular intervals in a circumferential direction around the axis of the light source supporter 10 when viewed in the Z direction. Further, in a static state where the light source supporter 10 and the tubular body 12 have not been deformed, the tips of the supporting projections 12p may or may not be in contact with the inner wall surface 10a of the light source supporter 10. Further, the supporting projections 12p may be formed so as to project from the light source supporter 10 toward the tubular body 12.

Further, the tubular body 12 has gap-maintaining parts 12q formed so as to project from the inner tubular body 12a toward the outer tubular body 12b. As shown in FIG. 2, similarly to the supporting projections 12p described above, three gap-maintaining parts 12q are formed. These gap-maintaining parts 12q are spaced at regular intervals in a circumferential direction around the axis of the light source supporter 10 when the light source supporter 10 is viewed in the Z direction.

The gap-maintaining parts 12q are configured so that only the tips thereof come into contact with the inner wall surface 30a of the outer tubular body 12b to maintain the air gap 12s when the inner tubular body 12a and the outer tubular body 12b are deformed by, for example, flowing of the cooling water (W1, W2) or thermal expansion.

It is to be noted that the number of the gap-maintaining parts 12q is not particularly limited, the gap-maintaining parts 12q do not necessarily have to be spaced at regular intervals in a circumferential direction around the axis of the light source supporter 10 when viewed in the Z direction, the number of the gap-maintaining parts 12q does not necessarily have to be the same as the number of the supporting projections 12p, and the gap-maintaining parts 12q do not necessarily have to be formed in the same radial directions as the supporting projections 12p when viewed from the axis of the light source supporter 10.

Further, in a rest state where the light source supporter 10 and the tubular body 12 have not been deformed, the tips of the gap-maintaining parts 12q may or may not be in contact with the inner wall surface 30a of the outer tubular body 12b. Further, the gap-maintaining parts 12q may be formed so as to project from the outer tubular body 12b toward the inner tubular body 12a.

Further, the tubular body 12 is spaced from the light source supporter 10 on the end 10e side of the light source supporter 10, and therefore the first flow channel F1 and the second flow channel F2 communicate with each other on the end 10e side of the light source supporter 10. Such a structure allows the cooling water W1 supplied from an inlet 13a to the second flow channel F2 to flow through the second flow channel F2 in the −Z direction, then flow through the first flow channel F1 in the +Z direction while absorbing heat from the light-emitting elements 11, and then be discharged from the outlet 10h as the cooling water W2.

In the light irradiation device 1 according to the present invention, the above-described flow of the cooling water (W1, W2) may be reversed. That is, the part used as the inlet 13a and the part used as the outlet 10h in the above structure may be used as an outlet and an inlet respectively so that the cooling water W1 supplied from the inlet to the first flow channel F1 flows through the first flow channel F1 in the −Z direction while absorbing heat from the light-emitting elements 11, then flows through the second flow channel F2 in the +Z direction, and is then discharged from the outlet as the cooling water W2.

Figure 3:
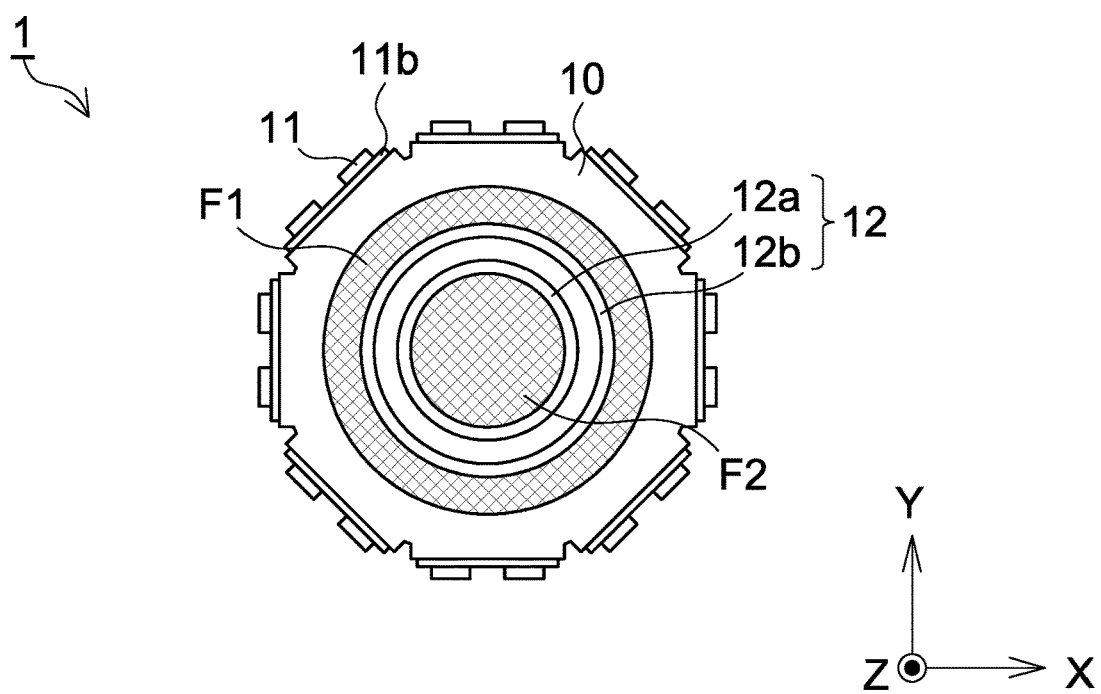
FIG. 3 is a sectional view of the light irradiation device shown in FIG. 1 taken along an XY plane at a predetermined Z coordinate.

Further, the first flow channel F1 is formed so that the flow channel cross-sectional area of the first flow channel F1 as viewed in the Z direction is smaller than that of the second flow channel F2 as viewed in the Z direction. FIG. 3 is a sectional view of the light irradiation device 1 shown in FIG. 1 taken along an XY plane at a predetermined Z coordinate. The flow channel cross-sectional area of each of the flow channels (F1, F2) as viewed in the Z direction refers to the cross-sectional area of each of the flow channels (F1, F2) when the light irradiation device 1 is taken along an XY plane orthogonal to the Z direction as indicated by hatching in FIG. 3.

As described above, the flow velocity of the cooling water W2 flowing through the first flow channel F1 can be made faster than that of the cooling water W1 flowing through the second flow channel F2 by making the flow channel cross-sectional area of the first flow channel F1 smaller than that of the second flow channel F2, which improves the efficiency of cooling the light-emitting elements 11.

As shown in FIG. 1, an example of the structure of the present embodiment has an outer diameter φ1 of the first flow channel F1 (a diameter of the inner wall surface 10a of the light source supporter 10) of 45 mm, an inner diameter φ2 of the first flow channel F1 (a diameter of the outer wall surface 30b of the outer tubular body 12b) of 40 mm, and a diameter φ3 of the second flow channel F2 (a diameter of the inner wall surface 20a of the inner tubular body 12a) of 24 mm.

In such a structure, the flow channel cross-sectional area of the first flow channel F1 as viewed in the Z direction is 334 mm$^2$, and the flow channel cross-sectional area of the second flow channel F2 as viewed in the Z direction is 452 mm$^2$, that is, the flow channel cross-sectional area of the first flow channel F1 as viewed in the Z direction is smaller than that of the second flow channel F2 as viewed in the Z direction. It is to be noted that the length of the light irradiation device 1 in the Z direction is 4 m.

Here, all the light source supporter 10, the inner tubular body 12a, and the outer tubular body 12b do not necessarily have to be made of the same material, but are preferably made of the same material for the reason that welding for preventing the leakage of the cooling water (W1, W2) can easily be performed or electrolytic corrosion is less likely to occur. Further, the material of the light source supporter 10 is not particularly limited as long as it has a thermal conductivity higher than that of air interposed between the first flow channel F1 and the second flow channel F2. As described above, for example, copper, stainless steel, or titanium may be used.

Figure 4:
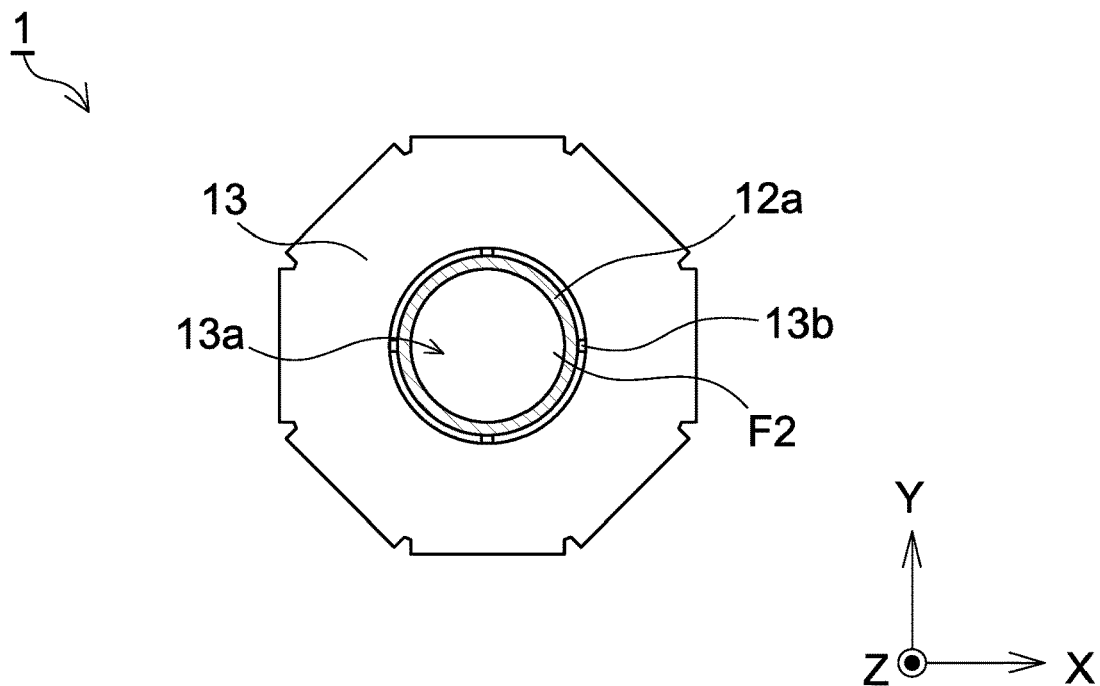
FIG. 4 is a side view of the light irradiation device shown in FIG. 1 as viewed in a −Z direction.
Figure 5:
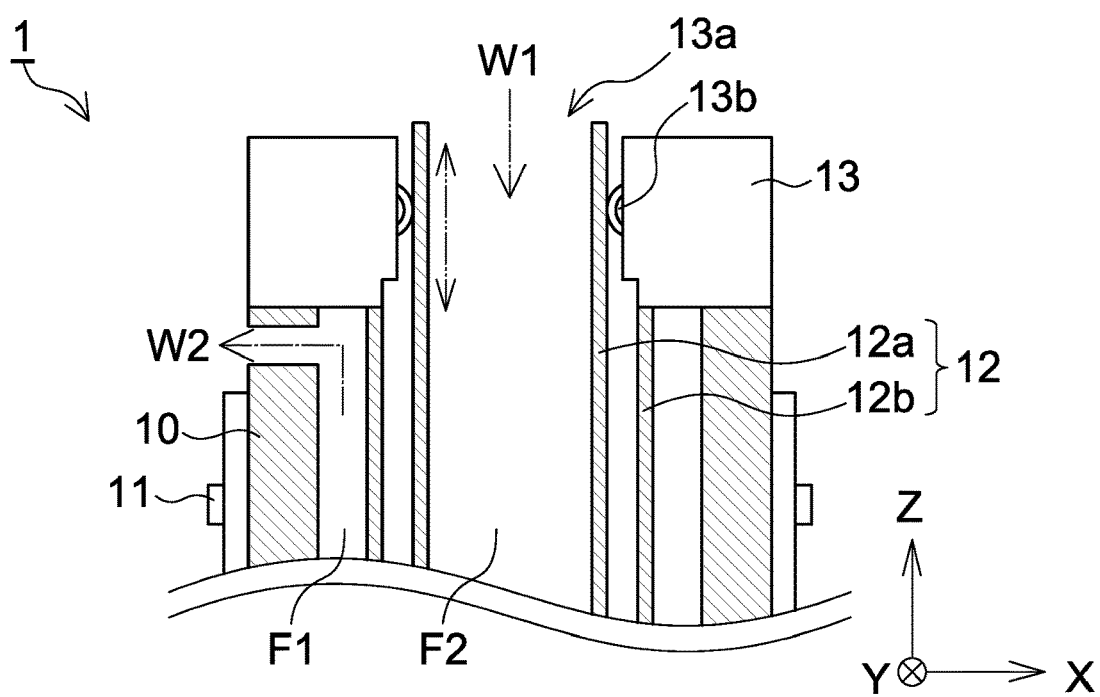
FIG. 5 is an enlarged view showing a holding member and its vicinity of the light irradiation device shown in FIG. 1.

FIG. 4 is a side view of the light irradiation device 1 shown in FIG. 1 as viewed in the −Z direction. FIG. 5 is an enlarged view showing the holding member 13 and its vicinity of the light irradiation device 1 shown in FIG. 1. As shown in FIG. 4 and FIG. 5, the holding member 13 has the inlet 13a, and rollers 13b are provided in part of the inlet 13a to support the inner tubular body 12a. The rollers 13b are in contact with the inner tubular body 12a so that the inner tubular body 12a and the outer tubular body 12b can slide in the Z direction. As described above, the holding member 13 is preferably made of a material having a certain degree of elasticity. For example, a synthetic resin such as a fluorine resin or polytetrafluoroethylene may be used.

The inner tubular body 12a and the outer tubular body 12b are thermally expanded by heat. Particularly, the inner tubular body 12a and the outer tubular body 12b are fixed by engagement on the end 10e side in the Z direction, and therefore if the inner tubular body 12a and the outer tubular body 12b fixed also by the holding member 13, the inner tubular body 12a and the outer tubular body 12b cannot expand or shrink independently in the Z direction.

Therefore, when a thermal expansion difference is caused in the Z direction between the inner tubular body 12a and the outer tubular body 12b, a heavy load is put on the connecting member 12c or the holding member 13, and in some cases, and these members may break.

Such a structure as described above, however, allows the inner tubular body 12a and the outer tubular body 12b to slide in the Z direction so that the inner tubular body 12a and the outer tubular body 12b can expand or shrink independently from each other in the Z direction. That is, it is possible to reduce a load put on the connecting member 12c and the holding member 13 resulting from a thermal expansion difference in the Z direction between the inner tubular body 12a and the outer tubular body 12b.

The light irradiation device 1 having the above-described structure has improved cooling efficiency because the transfer of heat from the cooling water W2 flowing through the first flow channel F1 to the cooling water W1 flowing through the second flow channel F2 is suppressed. Further, the supporting projections 12p and the gap-maintaining parts 12q maintain the shape of the flow channel (F1, F2) and the shape of the air gap 12s interposed between the inner tubular body 12a and the outer tubular body 12b, which makes it possible to uniformly cool the light-emitting elements 11 throughout the light irradiation device 1.

Further, the light source supporter 10 and the tubular body 12 of the present embodiment are integrally formed of the same material, which reduces the number of joints between the members and eliminates the need for a structure for suppressing the leakage of the cooling water (W1, W2) such as an O ring.

Further, a load put on the connecting member 12c and the holding member 13 resulting from thermal expansion is reduced, and breakage of these members may be reduced. This makes it possible to significantly reduce time and effort required for maintenance of the light irradiation device 1 or eliminate the need for periodic maintenance of the light irradiation device 1.

Another Embodiment

Hereinbelow, another embodiment will be described.

Figure 6:
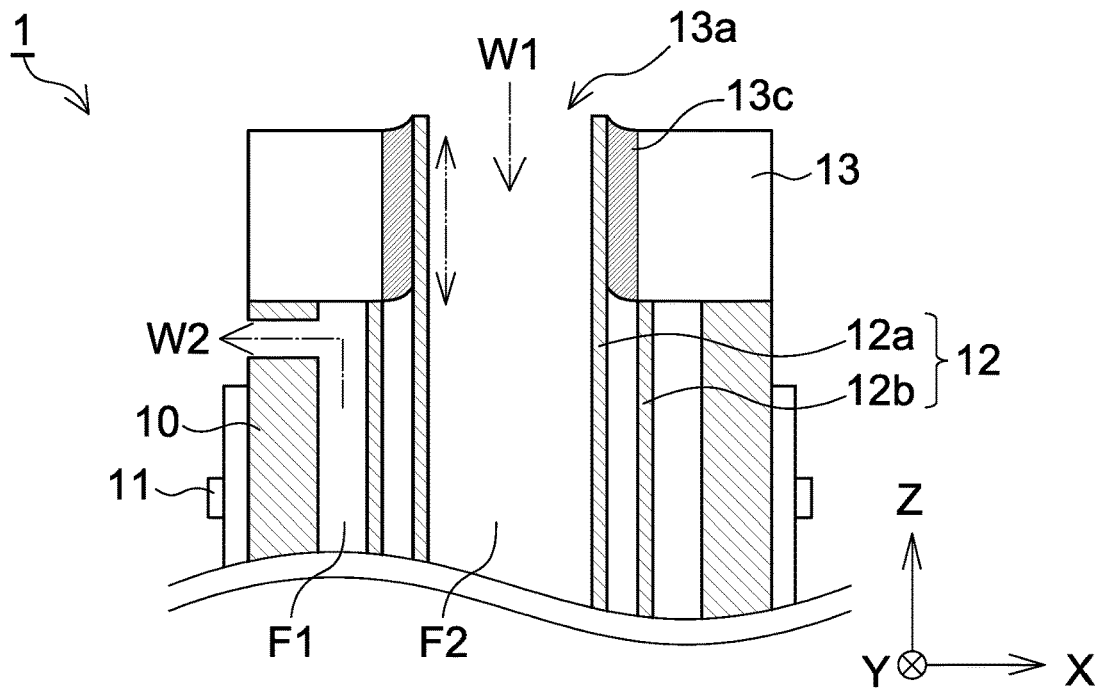
FIG. 6 is an enlarged view of a holding member and its vicinity of another embodiment of the light irradiation device.

<1> FIG. 6 is an enlarged view of the holding member 13 and its vicinity of another embodiment of the light irradiation device 1. As shown in FIG. 6, the holding member 13 may have an elastic member 13c so that the inner tubular body 12a is fixed by the elastic member 13c to relieve a thermal expansion difference in the Z direction between the inner tubular body 12a and the outer tubular body 12b.

Such a structure allows the inner tubular body 12a to be supported by the elastic member 13c, which makes it possible to relieve a load put on the connecting member 12c and the holding member 13 even when a thermal expansion difference is caused in the Z direction between the inner tubular body 12a and the outer tubular body 12b. It is to be noted that the holding member 13 may entirely be constituted from the elastic member 13c. As described above, the elastic member 13c may be a synthetic rubber such as a fluorine-containing rubber or a silicone resin.

<2> The tubular body 12 may be a member integrally formed of a material having a thermal conductivity lower than that of a material constituting the light source supporter 10 (the outer wall surface of the first flow channel F1). Further, the air gap 12s interposed between the inner tubular body 12a and the outer tubular body 12b of the tubular body 12 may be filled with a material having a thermal conductivity lower than that of a material constituting the light source supporter 10 (the outer wall surface of the first flow channel F1).

Such a structure in which a material having a thermal conductivity lower than that of a material constituting the light source supporter 10 (the outer wall surface of the first flow channel F1) is interposed between the first flow channel F1 and the second flow channel F2 reduces transfer of heat from the cooling water W2 flowing through the first flow channel F1 to the cooling water W1 flowing through the second flow channel F2. It is to be noted that the material filled in the air gap 12s may be any one of a solid, a liquid, and a gas.

Figure 7:
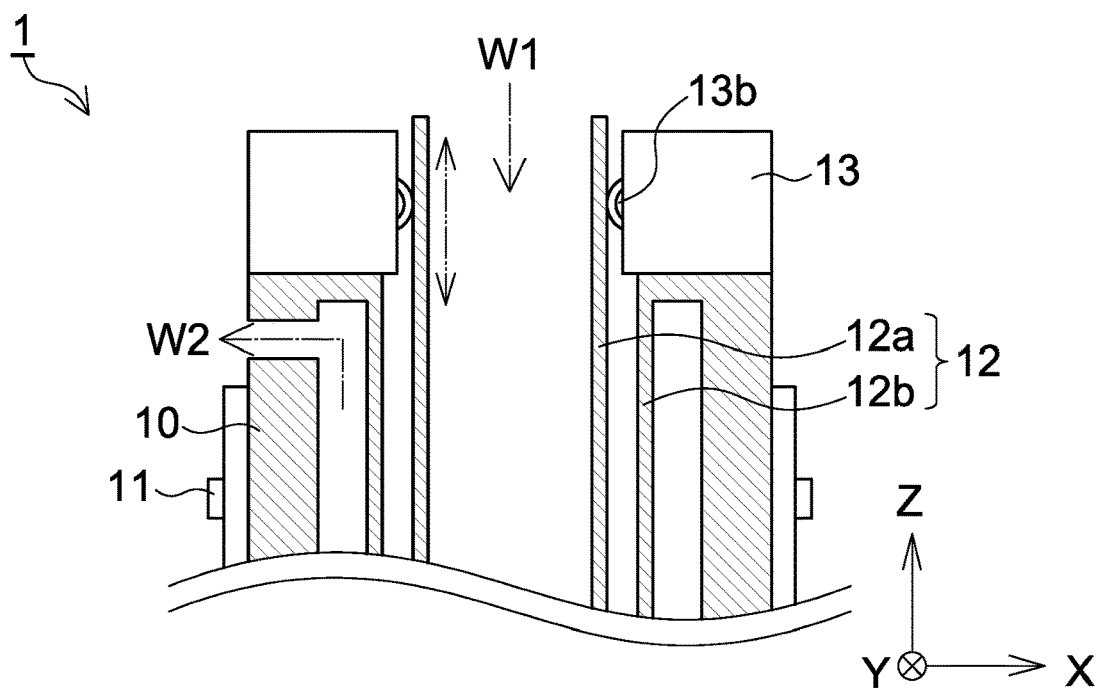
FIG. 7 is an enlarged view of a holding member and its vicinity of another embodiment of the light irradiation device.

<3> FIG. 7 is an enlarged view of the holding member 13 and its vicinity of another embodiment of the light irradiation device 1. As shown in FIG. 7, the light source supporter 10 and the outer tubular body 12b may integrally be formed so as to be joined together on the holding member 13 side.

Figure 8:
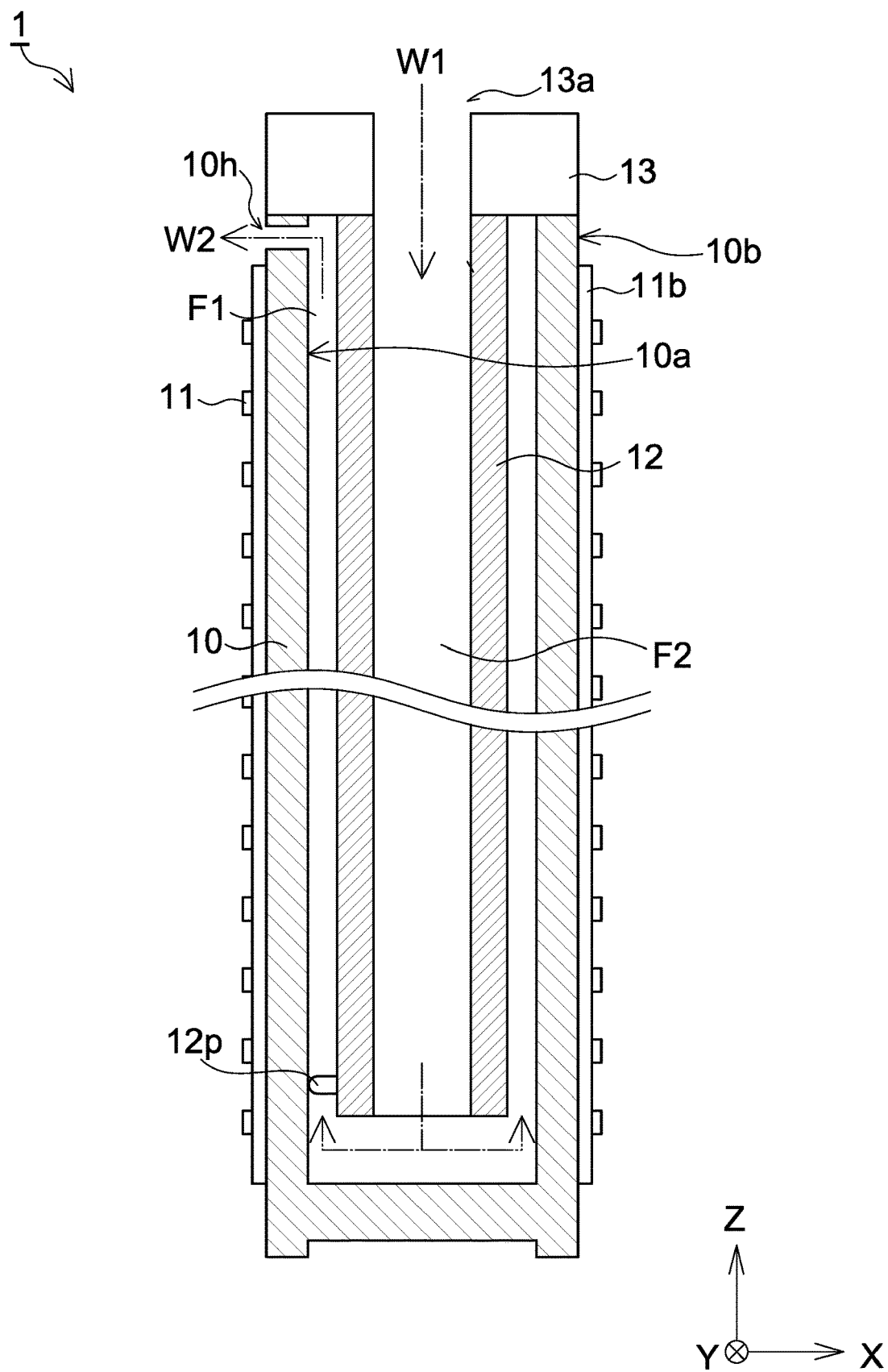
FIG. 8 is a schematic sectional side view of an embodiment of a light irradiation device.
Figure 9:
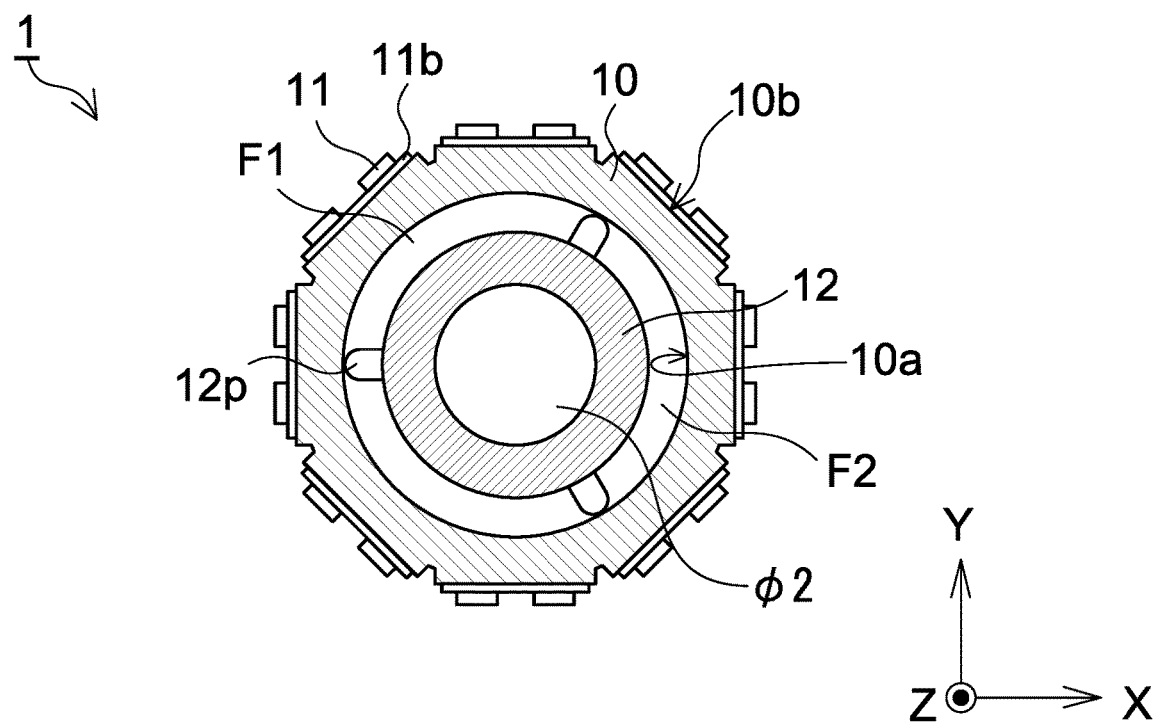
FIG. 9 is a sectional view of the light irradiation device shown in FIG. 8 taken along an XY plane at a predetermined Z coordinate.
Figure 10:
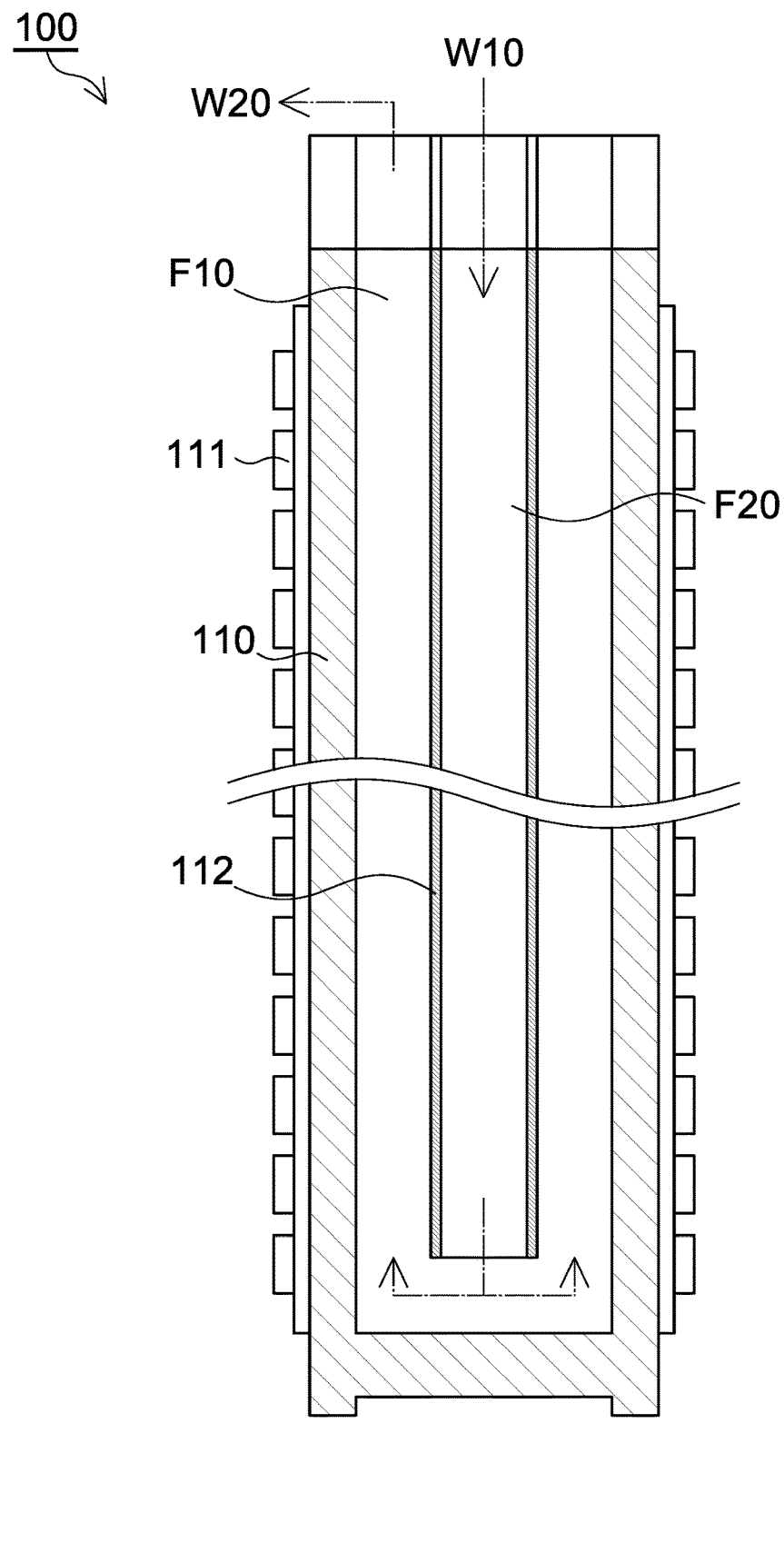
FIG. 10 is a schematic sectional side view of a light irradiation device having a conventional structure.
Figure 10:
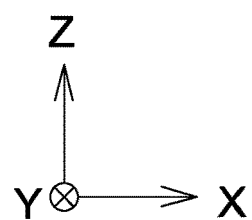
Figure 11:
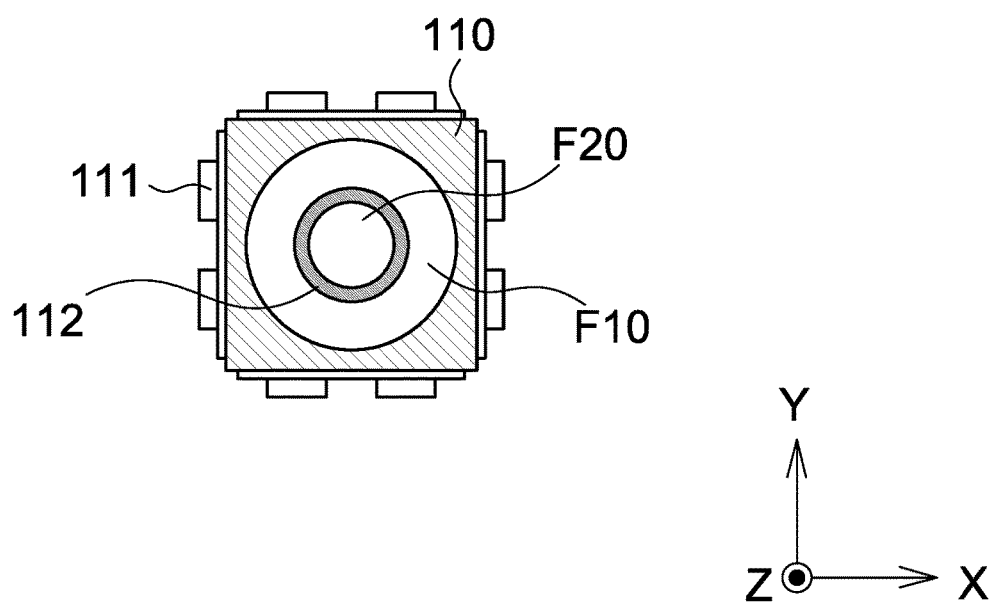
FIG. 11 is a sectional view of the light irradiation device shown in FIG. 10 taken along an XY plane at a predetermined Z coordinate.

<4> FIG. 8 is a schematic sectional side view of another embodiment of the light irradiation device 1. FIG. 9 is a sectional view of the light irradiation device 1 shown in FIG. 8 taken along an XY plane at a predetermined Z coordinate. As shown in FIG. 8 and FIG. 9, the tubular body 12 may integrally be formed of a material having a thermal conductivity lower than that of a material constituting the outer wall of the first flow channel F1.

<5> The above-described structures of the light irradiation device 1 are merely examples, and the present invention is not limited to the structures shown in the drawings.

What is claimed is:

1. A light irradiation device comprising:
   a light source supporter having a tubular shape is closed on a side of one end;
   a plurality of light-emitting elements placed on an outer wall surface of the light source supporter;
   a tubular body extending inside the light source supporter in an axial direction of the light source supporter;
   a first flow channel formed between the tubular body and the light source supporter and having an annular shape when viewed from the axial direction; and
   a second flow channel formed inside the tubular body, wherein
   the first flow channel and the second flow channel communicate with each other on the side of one end of the light source supporter, and
   the tubular body contains a material having a thermal conductivity lower than a thermal conductivity of a material constituting an outer wall of the first flow channel.

2. The light irradiation device according to claim 1, wherein a gap is interposed between the first flow channel and the second flow channel.

3. The light irradiation device according to claim 2, further comprising a plurality of supporting projections formed so as to project from the light source supporter toward the tubular body or from the tubular body toward the light source supporter.

4. The light irradiation device according to claim 1, further comprising a plurality of supporting projections formed so as to project from the light source supporter toward the tubular body or from the tubular body toward the light source supporter.

5. The light irradiation device according to claim 4, wherein a number of the supporting projections as viewed in the axial direction is at least three.

6. The light irradiation device according to claim 4, wherein the tubular body includes an inner tubular body having the second flow channel formed therein and an outer tubular body provided so as to surround the inner tubular body.

7. The light irradiation device according to claim 6, further comprising a plurality of gap-maintaining parts formed so as to project from the inner tubular body toward the outer tubular body or from the outer tubular body toward the inner tubular body.

8. The light irradiation device according to claim 7, wherein a number of the gap-maintaining parts as viewed in the axial direction is at least three.

9. The light irradiation device according to claim 7, further comprising a holding member having a function of fixing the light source supporter and the tubular body at an end opposite to the one end of the light source supporter and relieving a thermal expansion difference in the axial direction between the inner tubular body and the outer tubular body.

10. The light irradiation device according to claim 6, further comprising a holding member having a function of fixing the light source supporter and the tubular body at an end opposite to the one end of the light source supporter and relieving a thermal expansion difference in the axial direction between the inner tubular body and the outer tubular body.

11. The light irradiation device according to claim 10, wherein the holding member has a mechanism configured to allow the inner tubular body and the outer tubular body to slide along the axial direction.

12. The light irradiation device according to claim 10, wherein the holding member has an elastic member to allow the inner tubular body and the outer tubular body to be displaced along the axial direction.

13. The light irradiation device according to claim 10, wherein the outer wall of the first flow channel, the inner tubular body, and the outer tubular body are made of a same material.

14. The light irradiation device according to claim 10, wherein a flow channel cross-sectional area of the first flow channel as viewed in the axial direction is smaller than a flow channel cross-sectional area of the second flow channel as viewed in the axial direction.

15. The light irradiation device according to claim 6, wherein the outer wall of the first flow channel, the inner tubular body, and the outer tubular body are made of the same material.

16. The light irradiation device according to claim 6, wherein a flow channel cross-sectional area of the first flow channel as viewed in the axial direction is smaller than a flow channel cross-sectional area of the second flow channel as viewed in the axial direction.

17. The light irradiation device according to claim 4, wherein a flow channel cross-sectional area of the first flow channel as viewed in the axial direction is smaller than a flow channel cross-sectional area of the second flow channel as viewed in the axial direction.

18. The light irradiation device according to claim 1, wherein a flow channel cross-sectional area of the first flow channel as viewed in the axial direction is smaller than a flow channel cross-sectional area of the second flow channel as viewed in the axial direction.

* * * * *